(12) United States Patent
Boese

(10) Patent No.: US 7,267,838 B2
(45) Date of Patent: Sep. 11, 2007

(54) METHOD FOR APPLYING A FILM OF SAMPLE TO A SAMPLE CARRIER

(75) Inventor: Matthias Boese, Kämpfelbach (DE)

(73) Assignee: Bruker BioSpin, GmbH, Rheinstetten-Furchheim (DE)

( * ) Notice: Subject to any disclaimer, the term of this patent is extended or adjusted under 35 U.S.C. 154(b) by 613 days.

(21) Appl. No.: 10/675,804

(22) Filed: Sep. 30, 2003

(65) Prior Publication Data

US 2004/0113072 A1   Jun. 17, 2004

(30) Foreign Application Priority Data

Oct. 4, 2002   (DE) ................ 102 46 446

(51) Int. Cl.
   *B05D 5/00*   (2006.01)
   *B05D 3/00*   (2006.01)
   *B05D 3/06*   (2006.01)

(52) U.S. Cl. .............. 427/8; 427/265; 427/287; 427/372.2

(58) Field of Classification Search ............ 427/2.11, 427/8, 541, 372.2, 256, 258, 261, 265, 266, 427/269, 287
See application file for complete search history.

(56) References Cited

U.S. PATENT DOCUMENTS 5,770,860 A   6/1998   Franzen

2003/0143316 A1*   7/2003   Eipel et al. ............... 427/2.11

FOREIGN PATENT DOCUMENTS

| DE | 40 24 545 A1 | 6/1992 |
|----|----|----|
| DE | 196 28 928 A1 | 7/1996 |
| DE | 197 42 246 A1 | 9/1997 |
| DE | 198 17 531 A1 | 4/1998 |
| DE | 199 23 761 C1 | 5/1999 |

* cited by examiner

Primary Examiner—William Phillip Fletcher, III
(74) Attorney, Agent, or Firm—The Law Offices of Paul E. Kudirka

(57) ABSTRACT

A method for applying a sample film to a sample carrier for subsequent spectroscopic analysis is described, comprising providing a quantity of sample in liquid state, providing a sample carrier having at least one sample position, applying the quantity of sample in liquid state on the at least one sample position in a plurality of partial quantities of the quantity of sample in such a manner that the partial quantities on the at least one sample position are not in contact with one another before being dried, drying the quantity of sample to form the sample film.

18 Claims, 3 Drawing Sheets

METHOD FOR APPLYING A FILM OF SAMPLE TO A SAMPLE CARRIER

CROSS REFERENCE TO RELATED APPLICATION

The present application claims priority of German patent application 102 46 446.4, filed on Oct. 4, 2002.

BACKGROUND OF THE INVENTION

The invention relates to a method for applying a film of sample to a sample carrier for subsequent spectroscopic analysis.

In the context of spectroscopic sample analysis, in particular in the context of vibrational spectroscopy, such as for example IR, NIR, Raman spectroscopy, a method as mentioned above is used to prepare samples for the subsequent spectroscopic analysis.

The samples which are to be applied to the sample carrier may, for example, be biological liquids, such as serum, urine, suspended cells, cell culture media, etc. or analytes dissolved in water, which are subsequently to be analyzed and in particular quantified by IR spectroscopy.

On account of the high inherent absorption of some solvents in the infrared (IR) spectral region, the quantity of sample applied to the sample carrier in the liquid state is dried to form a film of sample prior to the spectroscopic measurement. This ideally leads to the formation of homogeneous films of sample, i.e. films of sample which have a uniform layer thickness, so that the Lambert-Beer law applies. However, this method of applying a film of sample by drying a quantity of sample applied in liquid form is unsuitable for many solvents, in particular water, since the film of sample which is formed by drying does not have a uniform layer thickness over the area of the sample position, but rather has a greater layer thickness toward the edge than in the center. This phenomenon is explained below with reference to FIGS. 3 and 4.

FIG. 3 illustrates a sample carrier 1 which has a sample position A to which a quantity of sample 2 in the liquid state has been applied. The quantity of sample typically has a volume of 1-100 μl, while the sample position A has a diameter of approximately 1-20 mm. The sample position A is the region of the sample carrier which, in the case, for example, of IR spectroscopy, is illuminated by the light beam during the subsequent spectroscopic analysis.

Now, if the quantity of sample, as illustrated in FIG. 3, is applied to the sample position A of the sample carrier 1 distributed uniformly in the form of a drop, the quantity of liquid sample, irrespective of whether it is applied manually using a pipette or with the aid of an automated pipetting device, in section forms approximately the shape of a half-oval on the sample position. The surface tension of the quantity of liquid sample in this case determines the precise shape of the half-oval.

After the quantity of sample 2 has been dried, what remains is a film of sample 3 which is significantly thicker at the edges than in the center, as illustrated in FIG. 4. Accordingly, the film of sample 3 has a crater-like appearance. This cratering effect is particularly pronounced if the solvent used for the sample is water. The layer thickness of the film of sample 3 formed is therefore not homogeneous across the sample position A.

It has emerged that when the same sample and the same quantity of sample are repeatedly discharged onto a plurality of sample positions, the films of sample which are formed after drying also often adopt different forms. This means that the known method for applying a film of sample to a sample carrier not only leads to an inhomogeneous layer thickness in each individual film of sample, but also leads to very different spectra, which may differ significantly in particular in terms of their signal intensity, being obtained during a spectroscopic analysis of a plurality of films of sample which have been produced from the same sample batch. Therefore, the conventional method has the drawback that the films of sample cannot be produced in an unambiguously reproducible way.

SUMMARY OF THE INVENTION

Therefore, it is an object of the invention to provide a method for applying a sample film to a sample carrier, in particular a method which renders it possible that sample films from the same sample batch can be produced reproducibly, such that the subsequent spectroscopic analysis gives reliable results.

According to one aspect of the invention, a method for applying a sample film to a sample carrier for subsequent spectroscopic analysis is provided, comprising:
providing a quantity of sample in liquid state;
providing a sample carrier having at least one sample position;
applying the quantity of sample in liquid state on the at least one sample position in a plurality of partial quantities of the quantity of sample in such a manner that the partial quantities on the at least one sample position are not in contact with one another before being dried;
drying the quantity of sample to form the sample film.

Now, instead of a quantity of sample being distributed uniformly in one step over the sample position which subsequently forms the measurement area for the spectroscopic analysis, as is the case in the conventional procedure, in the method according to the invention a quantity of liquid sample is to be applied to the sample position of the sample carrier in a large number of partial quantities, i.e. in small portions, in such a manner that the individual partial quantities of the quantity of sample are not in contact with one another. Accordingly, a large number of small disjunct droplets of the sample are applied to the sample position and are then dried to form the sample film without mixing with one another. Although the cratering effect described above occurs with each of these partial quantities after they have been dried, the fact that a large number of these partial quantities are distributed over the sample position means that this cratering effect evens itself out over the area of the sample position, so that the sample film which is formed after the partial quantities have dried on the sample position is considerably more homogeneous as seen over the overall area of the sample position than if the quantity of sample is applied in its entirety in a single step to the sample position.

In a preferred refinement of the method, the partial quantities are applied to the sample position in the form of a fine grid with a maximum occupation density.

An advantage in this context is that the film of sample which is formed after the partial quantities have dried has an optimum homogeneity in terms of its layer thickness on account of the partial quantities being arranged in the form of a fine grid on the sample position with a maximum occupancy density, without the partial quantities being mixed with one another. Commercially available pipetting robots, which automatically apply the large number of partial quantities to the surface of the sample position of the sample carrier without them coming into contact with one another after they have been applied and thereby combining with one another, can be used to apply the large number of partial quantities in a grid-like arrangement.

In a further preferred refinement, the individual partial quantities amount to from 1/10,000 to 1/10 of the quantity of sample which is to be applied to the sample position.

The smaller the partial quantities, the higher the occupancy density of the partial quantities on the sample position can be and the more homogeneous the layer thickness of the film of sample formed after the partial quantities have dried becomes.

In a further preferred refinement, first of all a first layer of partial quantities is applied to the sample position, and after the first layer has dried, at least one further layer of partial quantities is applied and dried.

This measure is advantageous if the quantity of sample which is to be applied to the sample position cannot be applied to the sample position of the sample carrier in one layer. Furthermore, this measure has the advantage that overall a greater quantity of sample can be applied to the sample position of the sample carrier, in order to increase the sensitivity of the subsequent spectroscopic analysis.

In this context, it is preferable for the partial quantities belonging to the at least one further layer to be arranged on the sample position such that they are offset with respect to the positions of the partial quantities belonging to the first layer.

This measure has the advantage that the surface occupancy of the film of sample on the sample position of the sample carrier can be improved still further, i.e. no areas on which there is no film of sample remain on the sample position.

As an alternative to the refinement described above, it is also preferable if the partial quantities belonging to the at least second layer are applied to the position of the partial quantities belonging to the first layer.

This procedure has the advantage that application of the second layer of partial quantities of the quantity of sample cannot cause the partial quantities belonging to the first layer to become smeared or mixed as a result of the first layer which has already dried being partially dissolved, since such partial dissolution and mixing may under certain circumstances prove impossible to control, and this could have an adverse effect on the spectroscopic analysis.

In a further preferred refinement, the sample carrier is heated before, during or after the application of the partial quantities.

In this context, it is advantageous that the method according to the invention can overall be carried out in a shorter time, in particular if the quantity of sample is applied to the sample position of the sample carrier in a plurality of layers of partial quantities. This is because heating the sample carrier allows the drying of the partial quantities to be accelerated, so that in particular if a plurality of sample quantities are applied to various sample positions of a sample carrier application of the second layer of partial quantities to the first sample position can be continued as soon as one layer of partial quantities has just been applied to the final sample position of the sample carrier.

In further preferred refinements, a plate made in particular from IR-transparent material is used as the sample carrier, or alternatively the sample carrier used is a plate preferably made from metal or with a metallic surface whose surface is roughened.

In the former case, the method according to the invention is suitable for the preparation of samples for spectroscopic analysis of samples by transmission measurement, i.e. by measuring the light which passes through the sample carrier, in which case materials such as silicon, zinc selenide, calcium fluoride, barium fluoride, thallium bromide and germanium can be used for the sample carrier. In the latter case, the method according to the invention is suitable for the preparation of samples for spectroscopic analysis by means of diffuse reflection measurement at the roughened surface of the sample carrier.

Furthermore, the method according to the invention is particularly suitable when using microtiter plates which have a large number of sample positions, for example 96, 384 or 1536 positions.

The method according to the invention can be used to apply films of the same sample to the sample carrier in a very homogeneous and reproducible way, so that in the event of repeated discharge of the same sample, the spectra obtained in the subsequent spectroscopic analysis give reliable and reproducible results.

Further advantages and features will emerge from the following description and the appended drawing.

It will be understood that the features which have been mentioned above and those which are yet to be explained below can be used not only in the combination indicated in each instance but also in other combinations or on their own, without departing from the scope of the present invention.

BRIEF DESCRIPTION OF THE DRAWINGS

An exemplary embodiment of the invention is illustrated in the drawings and is described in more detail below with reference to the drawings, in which.

DETAILED DESCRIPTION OF A PREFERRED EMBODIMENT

Figure 1:
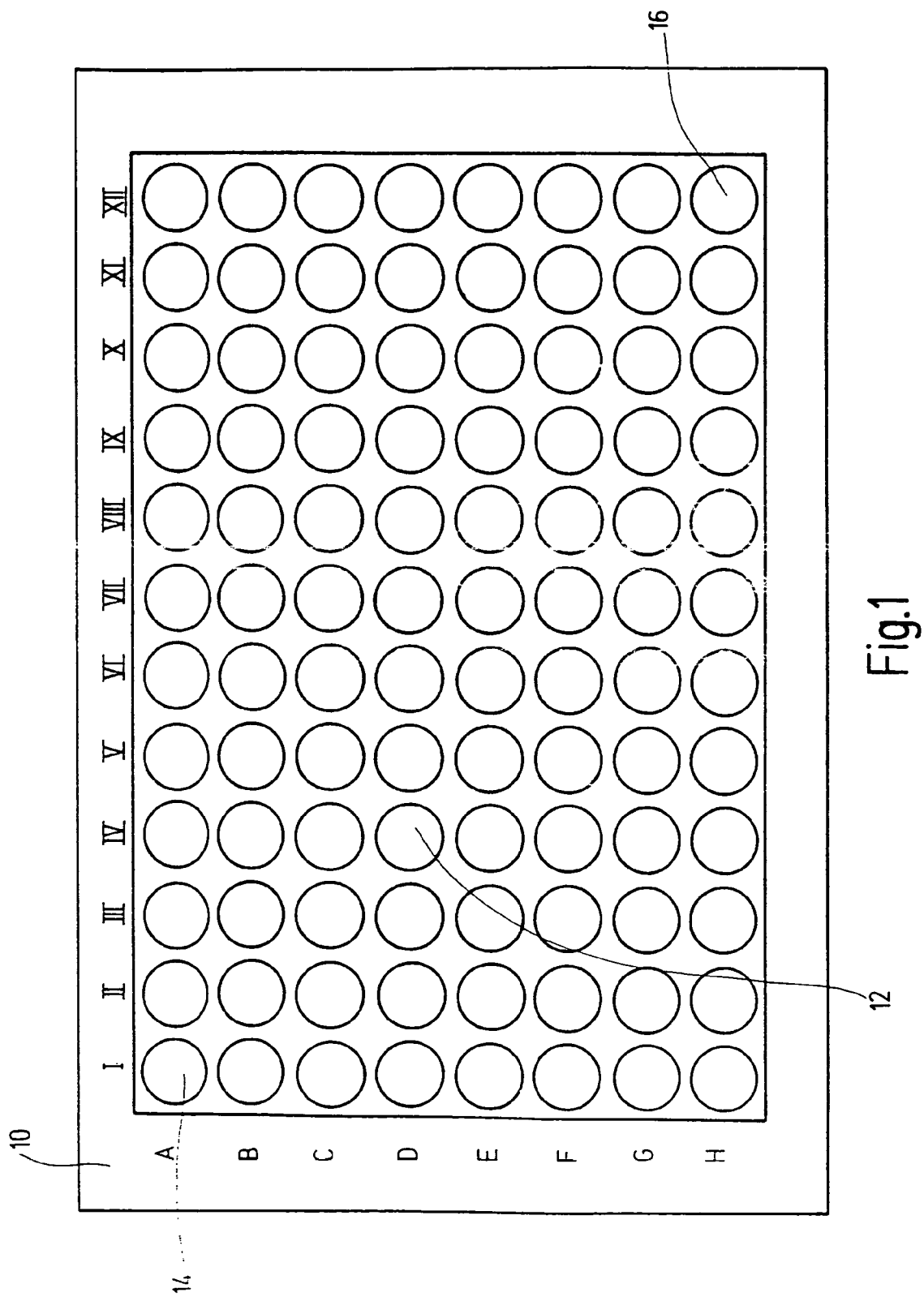
FIG. 1 diagrammatically depicts a sample carrier having a multiplicity of sample positions in plan view.

FIG. 1 illustrates a sample carrier 10, which is designed in the form of a microtiter plate with a total of 96 sample positions 12. The sample positions 12 are arranged in eight rows, denoted by A to H, and twelve columns, denoted by I to XII. A first sample position "I A" is provided with reference numeral 14, and a last sample position "XII H" is provided with reference numeral 16.

A sample film can be applied to each of the sample positions 12, in a manner which is described below, for subsequent spectroscopic analysis of the sample. The subsequent spectroscopic analysis in this case consists, for example, in an infrared (IR), near-infrared (NIR) or Raman spectroscopic analysis.

The method described below for applying sample films to the sample positions 12 of the sample carrier 10 is suitable in particular for samples in aqueous solutions, such as biological liquids, for example serum, urine, suspended cells, cell culture media, etc., or analytes dissolved in water, which are then to be quantified, for example by IR spectroscopy.

Depending on whether the optical spectroscopic analysis is to be carried out by transmission or reflection, in particular diffuse reflection, the sample carrier 10, at least in the region of the sample positions 12, is a plate made from in particular infrared-transparent material or has a roughened metallic surface.

To apply sample films which are subsequently to be analyzed by spectroscopy to the sample positions 12, the procedure described below with reference to the example of sample position 12 is preferably employed.

Figure 2:
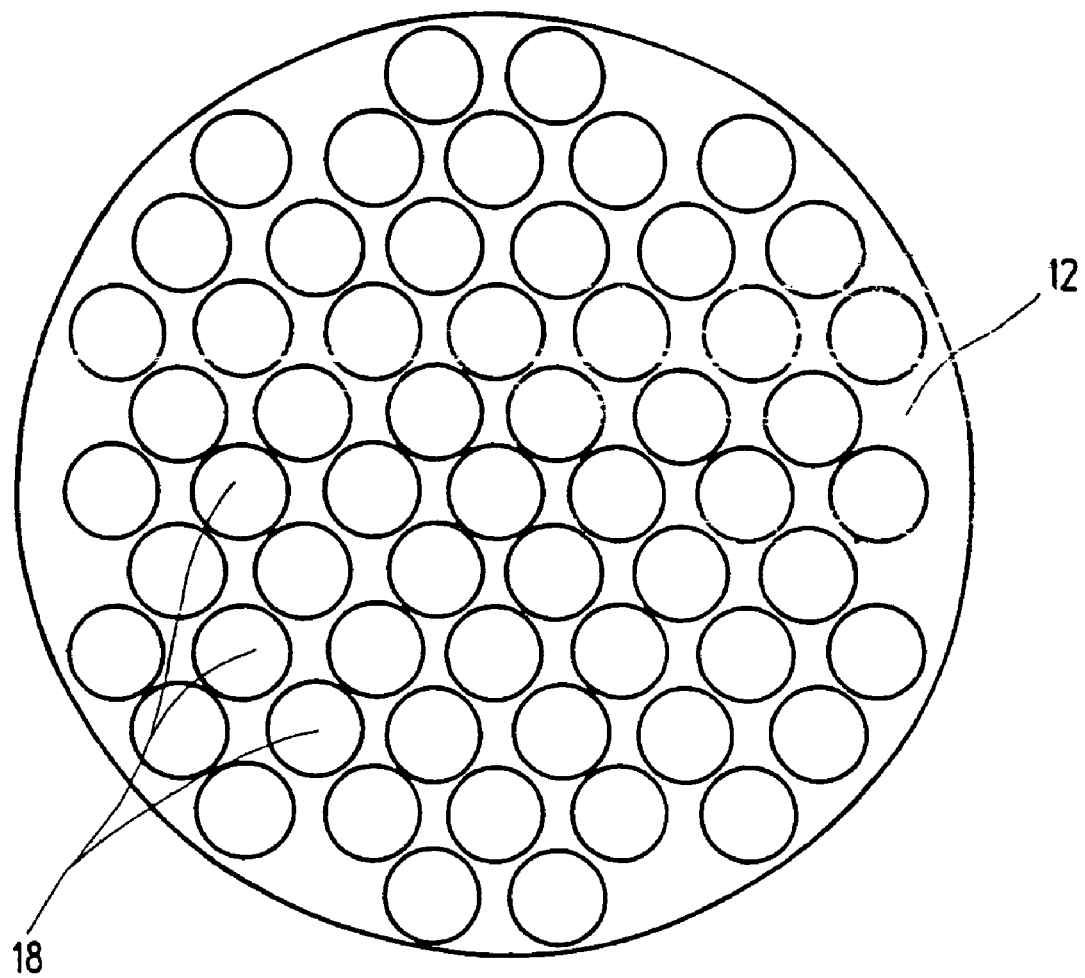
FIG. 2 shows a plan view of a greatly enlarged illustration of a single sample position of the sample carrier shown in FIG. 1, illustrating the method according to the invention.
Figure 3:
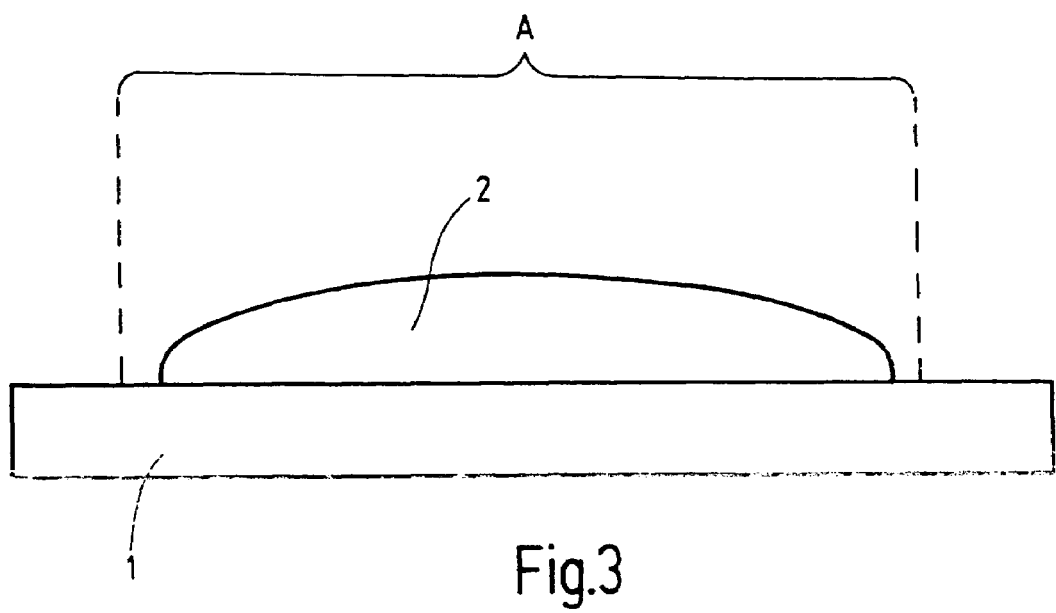
FIG. 3 diagrammatically depicts a sample carrier with a sample position in which a quantity of sample has been applied in the liquid state using the conventional method.
Figure 4:
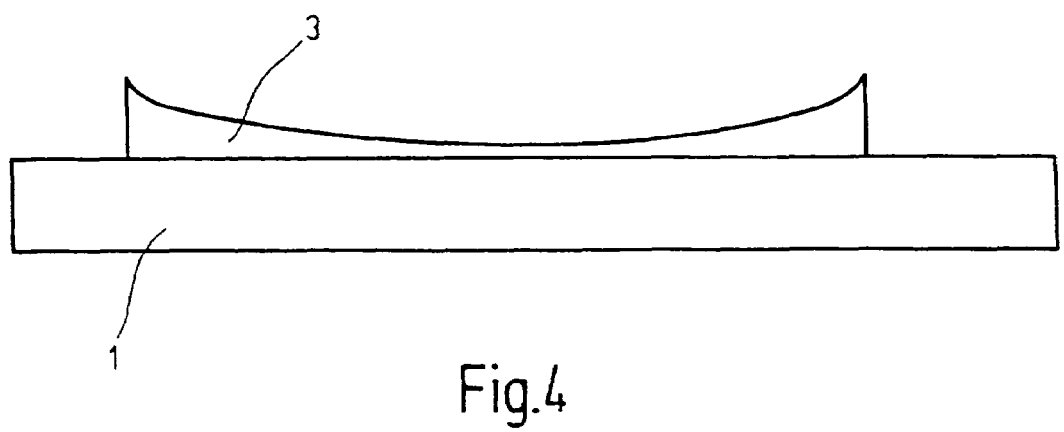
FIG. 4 shows an illustration which is similar to that shown in FIG. 3 after a film of sample has been formed from the quantity of liquid sample shown in FIG. 3 by drying in accordance with the standard method.

The quantity of sample which is to be applied to sample position 12 is applied to sample position 12 in the liquid state, this quantity of sample not being applied to the sample position 12 all at once or in a single step, but rather in a plurality of partial quantities 18, as illustrated in FIG. 2, without the partial quantities 18 coming into contact with one another, meaning that they cannot therefore mix with one another. These partial quantities 18 are then dried on the sample position 12 of the sample carrier 10 to form the film of the sample.

The individual partial quantities 18 represent small portions or droplets of the quantity of sample which is to be applied to the sample position 12 and are arranged in the form of a fine grid. A commercially available pipetting robot or microdispenser, which automatically applies the large number of partial quantities 18 to the entire surface of the sample position 12 of the sample carrier 10 in the form of small droplets with an individual volume of typically 1 to 500 nl, without the partial quantities 18 coming into contact with one another after they have been applied to the sample position 12 and fusing together, can be used to apply the individual partial quantities 18 to the sample position 12. The total sample quantity which results from the partial quantities 18 is approximately 1 to 100 µl. The partial quantities 18 individually amount to approximately $\frac{1}{10}$ to $\frac{1}{10,000}$ of the total sample quantity.

The individual partial quantities are applied to the sample position 12 with a maximum occupancy density. The largest possible part of the available surface area of the sample position 12 should be covered by the partial quantities 18, which then dry separately from one another, i.e. without coming into contact with one another.

To achieve maximum coverage of the sample position 12 with the sample which is then to be analyzed, the smallest possible volumes are used for the partial quantities 18. The smaller the partial quantities 18 or volumes of the droplets are, the more homogeneous the later thickness of the film of sample produced after the partial quantities 18 have dried becomes.

If it should prove impossible to pipette the quantity of sample which is to be applied to the sample position 12 in one layer, it is possible first of all to apply a first layer of partial quantities 18 to the sample position 12 and to dry this first layer, and then to apply further layers of partial quantities 18 and dry them after the first layer of these partial quantities 18 has dried. The one or more further layers of partial quantities 18 are in this case applied as accurately as possible to the positions of the partial quantities 18 or dried spots of sample formed by these partial quantities 18 belonging to the first layer, in order not to effect uncontrollable mixing of partial quantities 18 belonging to the first layer, which could be produced by these spots of sample being partially dissolved by the application of the further layers.

In this way, it is possible to gradually produce any desired layer thicknesses, so that the sensitivity of the subsequent spectroscopic analysis can be increased.

Referring once again to FIG. 1, all 96 sample positions 12 of the sample carrier 10 can be provided with films of sample in the manner described above. In this case, first of all, starting at sample position 14 or a subsequent sample position, all the sample positions 12 up to the last sample position 16 are successively provided with a first layer of partial quantities 18 of the respective sample quantity of the sample which is to be analyzed in each case. When the final sample position 16 has been reached in this way, the first layer of partial quantities 18 on the first sample position 14 has already dried, so that the second layer of partial quantities 18 of the corresponding quantity of sample can immediately be applied at sample position 14.

In this case, the drying time for each application can be optimally adjusted by heating the sample carrier 10 to a defined temperature, so that drying is accelerated.

What is claimed is:

1. A method of optical spectroscopy of samples, comprising the steps of:
   providing a quantity of sample in liquid state; providing a sample carrier having at least one sample position;
   applying said quantity of sample in liquid state on said at least one sample position in a plurality of partial quantities of said quantity of sample across a measurement area of said at least one sample position in such a manner that said partial quantities across said measurement area of said at least one sample position are not in contact with one another before being dried;
   drying said quantity of sample to form a sample film across said measurement area; and
   spectroscopically analyzing said sample film across said measurement area employing at least one of infrared spectroscopy, near infrared spectroscopy and Raman spectroscopy.

2. The method of claim 1, wherein said partial quantities of said quantity of sample are applied across said measurement area of said at least one sample position in form of a grid with a maximum occupation density.

3. The method of claim 1, wherein said partial quantities amount to from about $\frac{1}{10,000}$ to about $\frac{1}{10}$ of said quantity of sample to be applied to said at least one sample position.

4. The method of claim 1, wherein said applying said quantity of sample in liquid state across said measurement area of said at least one sample position comprises first applying a first layer of said partial quantities to said at least one sample position, drying said first layer and applying at least one further layer of partial quantities of said quantity of sample to said at least one sample position and drying said at least one further layer of partial quantities.

5. The method of claim 4, further comprising applying said partial quantities belonging to said at least one further layer to said at least one sample position such that said partial quantities of said at least one further layer are offset with respect to positions of said partial quantities belonging to said first layer.

6. The method of claim 5, further comprising heating said sample carrier.

7. The method of claim 5, wherein said plate is made from infrared (IR)-transparent material.

8. The method of claim 5, wherein a metal plate whose surface is roughened is used as said sample carrier.

9. The method of claim 5, wherein said sample carrier is used as a sample carrier having a plurality of sample positions.

10. The method of claim 1, wherein said applying said quantity of sample in liquid state on said at least one sample position comprises first applying a first layer of said partial quantities to said at least one sample position, drying said first layer and applying at least one further layer of partial quantities of said quantity of sample to said at least one sample position and drying said at least one further layer of partial quantities, wherein said partial quantities belonging to said at least one further layer are applied to positions of said partial quantities belonging to said first layer.

11. The method of claim 10, further comprising heating said sample carrier.

12. The method of claim 10, wherein a plate made from infrared transparent material is used as said sample carrier.

13. The method of claim 10, wherein a metal plate whose surface is roughened is used as said sample carrier.

14. The method of claim 10, wherein said sample carrier is used as a sample carrier having a plurality of sample positions.

15. The method of claim 1, further comprising heating said sample carrier.

16. The method of claim 1, wherein a plate made from infrared (IR)-transparent material is used as said sample carrier.

17. The method of claim 1, wherein a metal plate whose surface is roughened is used as said sample carrier.

18. The method of claim 1, wherein said sample carrier is used as a sample carrier having a plurality of sample positions.

* * * * *

UNITED STATES PATENT AND TRADEMARK OFFICE
CERTIFICATE OF CORRECTION

PATENT NO. : 7,267,838 B2  Page 1 of 1
APPLICATION NO. : 10/675804
DATED : September 11, 2007
INVENTOR(S) : Matthias Boese It is certified that error appears in the above-identified patent and that said Letters Patent is hereby corrected as shown below:

Title Page item 73

Please replace "Bruker BioSpin, GmbH; Rheinstetten-Furchheim (DE)" with --Bruker Optik GmbH; Ettlingen, Germany--.

Signed and Sealed this

Eleventh Day of November, 2008

JON W. DUDAS
*Director of the United States Patent and Trademark Office*

UNITED STATES PATENT AND TRADEMARK OFFICE
CERTIFICATE OF CORRECTION

PATENT NO. : 7,267,838 B2 Page 1 of 1
APPLICATION NO. : 10/675804
DATED : September 11, 2007
INVENTOR(S) : Matthias Boese It is certified that error appears in the above-identified patent and that said Letters Patent is hereby corrected as shown below:

Title Page item 73

Please replace "Bruker BioSpin, GmbH; Rheinstetten-Furchheim (DE)" with --Bruker Optik GmbH; Ettlingen, Germany--.

Signed and Sealed this

Twenty-fifth Day of November, 2008

JON W. DUDAS
*Director of the United States Patent and Trademark Office*